United States Patent (10) Patent No.: US 8,427,431 B2
Beck et al. (45) Date of Patent: Apr. 23, 2013

(54) OPERATOR CONTROL ELEMENT FOR A DEVICE, IN PARTICULAR A MEDICAL DEVICE

(75) Inventors: Werner Beck, Rückersdorf (DE); Klaus Bühler, Eckental-Eckenhaid (DE); Franz Meissner, Bamberg (DE)

(73) Assignee: Siemens Aktiengesellschaft, München (DE)

( * ) Notice: Subject to any disclaimer, the term of this patent is extended or adjusted under 35 U.S.C. 154(b) by 1384 days.

(21) Appl. No.: 11/596,729

(22) PCT Filed: May 13, 2005

(86) PCT No.: PCT/EP2005/052223
§ 371 (c)(1),
(2), (4) Date: Sep. 13, 2007

(87) PCT Pub. No.: WO2005/114530
PCT Pub. Date: Dec. 1, 2005

(65) Prior Publication Data
US 2008/0012833 A1 Jan. 17, 2008

(30) Foreign Application Priority Data
May 19, 2004 (DE) .......................... 10 2004 025 265

(51) Int. Cl.
*G06F 3/041* (2006.01)

(52) U.S. Cl.
USPC .......................................................... 345/173

(58) Field of Classification Search .......... 345/173–178; 600/300, 436, 440; 702/8, 134, 172; 715/763, 715/764, 773, 810, 862; 710/8, 10, 14
See application file for complete search history.

(56) References Cited

U.S. PATENT DOCUMENTS

| 4,710,758 | A | 12/1987 | Mussler et al. |
| 5,448,263 | A | 9/1995 | Martin |
| 5,471,226 | A | 11/1995 | Suzuki et al. |
| 5,988,851 | A * | 11/1999 | Gent ................................ 700/83 |
| 6,359,612 | B1 * | 3/2002 | Peter et al. ...................... 345/156 |
| 2003/0013959 | A1 | 1/2003 | Grunwald et al. |
| 2003/0038835 | A1 | 2/2003 | DeFelice |
| 2004/0061687 | A1 | 4/2004 | Kent et al. |
| 2005/0093831 | A1 * | 5/2005 | Wang ............................. 345/173 |

FOREIGN PATENT DOCUMENTS

| DE | 69526471 T2 | 2/1996 |
| EP | 0 664 505 A2 | 7/1995 |

* cited by examiner

Primary Examiner — Kevin M Nguyen

(57) ABSTRACT

The invention relates to an operating element for operating a device, especially an X-ray apparatus, in the form of a touch screen, said touch screen has a touch sensitive screen surface an is provided with a calibration routine for calibrating the touch screen. The invention is characterized in that during a start-up phase of the apparatus, the touch screen is configured in such a manner that it can be used as an activation element for activating the calibration routine.

11 Claims, 2 Drawing Sheets

OPERATOR CONTROL ELEMENT FOR A DEVICE, IN PARTICULAR A MEDICAL DEVICE

CROSS REFERENCE TO RELATED APPLICATIONS

This application is the US National Stage of International Application No. PCT/EP2005/052223, filed May 13, 2005 and claims the benefits of German Patent application No. 10 2004 025 265.3 filed May 19, 2004. All of the applications are incorporated by reference herein in their entirety.

FIELD OF INVENTION

The present invention relates to an operator control element for operating a device, in particular a medical device, the operator control element being formed by what is referred to as a touchscreen having a touch-sensitive screen surface.

BACKGROUND OF THE INVENTION

So-called touchscreens having a touch-sensitive surface have become established in recent times as input or operator control elements in the most diverse application areas, in particular also in medical application fields. The success of touchscreens in medical engineering is due in particular to the fact that the surface of a touchscreen as a smooth surface compared to the individual keys of a keyboard is significantly easier to clean and accordingly the hygiene requirements for medical equipment can be more effectively satisfied. Accordingly, increasing use is now being made, in particular in medical application areas, of devices in which the control operations are performed almost exclusively via a touchscreen and only individual switches are present for activating the overall apparatus.

Touchscreens in state-of-the-art implementations typically consist of a TFT display and a superimposed touch-sensitive film covering the display. Touching the film causes a change in an electric field. By evaluating said change it can be established at which point the film was touched. By an appropriate interaction between display and film it is then ensured that information shown on the display can be activated or selected by touching the corresponding point of the film.

However, due to variations in the signals and possible signs of aging in the electrodes used for generating the electric field, a certain discrepancy can arise over time between the touch-sensitive film and the display, as a result of which the operation of the touchscreen is made more difficult. In the worst case operation of the touchscreen can be made totally impossible thereby, because the keys shown on the display no longer coincide with the corresponding areas of the film or the film key areas come to lie completely outside the screen. In order to avoid or rectify this, a calibration or an adjustment of the touchscreen is required in which a calibration is performed by means of a specific touching of the film and evaluation of the signals being generated in the process, with the result that ultimately agreement is once again restored between what is shown on the display and the position calculated on the basis of the resulting signals when the screen is touched.

Touchscreens are normally shipped together with an adjustment program which allows a calibration to be performed in the above-described way. Said adjustment program is usually launched via a keyboard or a mouse connected to the device which enables said adjustment program to be easily invoked.

However, medical equipment is—as was already mentioned above—routinely shipped with as few separate input and operator control elements as possible, with the result that only the touchscreen as input element and a central on/off switch for the device are available to the end customer himself. Thus, only the touchscreen itself can be used to operate the medical device at the end customer site. However, if said touchscreen is decalibrated, there is the risk that no more functions at all can be activated, since due to the decalibration the operator control elements can no longer be correctly registered and accessed. In such a case the touchscreen would be totally unusable and would have to be sent back to the manufacturer for recalibration. Alternatively thereto it would also be possible to provide an additional input device such as a mouse or keyboard, a situation which should, however, be avoided due to the above-cited hygienic disadvantages of input devices of said kind.

SUMMARY OF INVENTION

The object underlying the present invention is thus to specify a means of initiating the calibration of a touchscreen in the simplest possible manner and in so doing dispense in particular with the need for an additional input device.

The object is achieved by an operator control element and by a method for operating a device by means of a touchscreen as claimed in the claims.

The solution according to the invention consists in using the touchscreen as an activating element for activating a calibration routine during a start phase of the device. Thus, when the device is started, the user is given the opportunity to decide whether a calibration is to be performed or not. According to a preferred exemplary embodiment of the present invention it is provided in this case that essentially the entire screen surface of the touchscreen serves as an activation element for activating the calibration routine, thereby ensuring that the calibration routine can still be invoked even in the event of a complete decalibration of the touchscreen.

As a calibration of the touchscreen is not required every time the device is started, it is provided according to a preferred variant that the possibility of activating the calibration routine exists only at the start of what is referred to as a service mode which is usually used in the course of maintenance activities to modify or reset operating parameters of the device.

As, furthermore, a recalibration of the touchscreen is not required every time the service mode is started either, it can additionally be provided that the user also has the option of skipping the calibration routine. For this purpose a specific area of the screen surface is used as a bypass element or, as the case may be, bypass key which, when activated, causes the calibration routine to be skipped and the actual service mode to be initiated immediately. Said bypass key takes up a significantly smaller area compared to the total screen surface and will also be able to be activated by the user only if the touchscreen is not already decalibrated. If that should in fact be the case, then due to the variations in the position calculation, touching the area of the film located above the displayed bypass key field would automatically be interpreted by the touchscreen controller as meaning that a calibration is to be performed.

The solution according to the invention thus opens up the possibility of initiating a calibration of the touchscreen without the use of an additional input or activation element. In particular it is ensured that the calibration routine can still be invoked even in the event of a totally decalibrated touchscreen.

BRIEF DESCRIPTION OF THE DRAWINGS

The invention shall be explained in more detail below with reference to the accompanying drawings, in which.

DETAILED DESCRIPTION OF INVENTION

Figure 1:
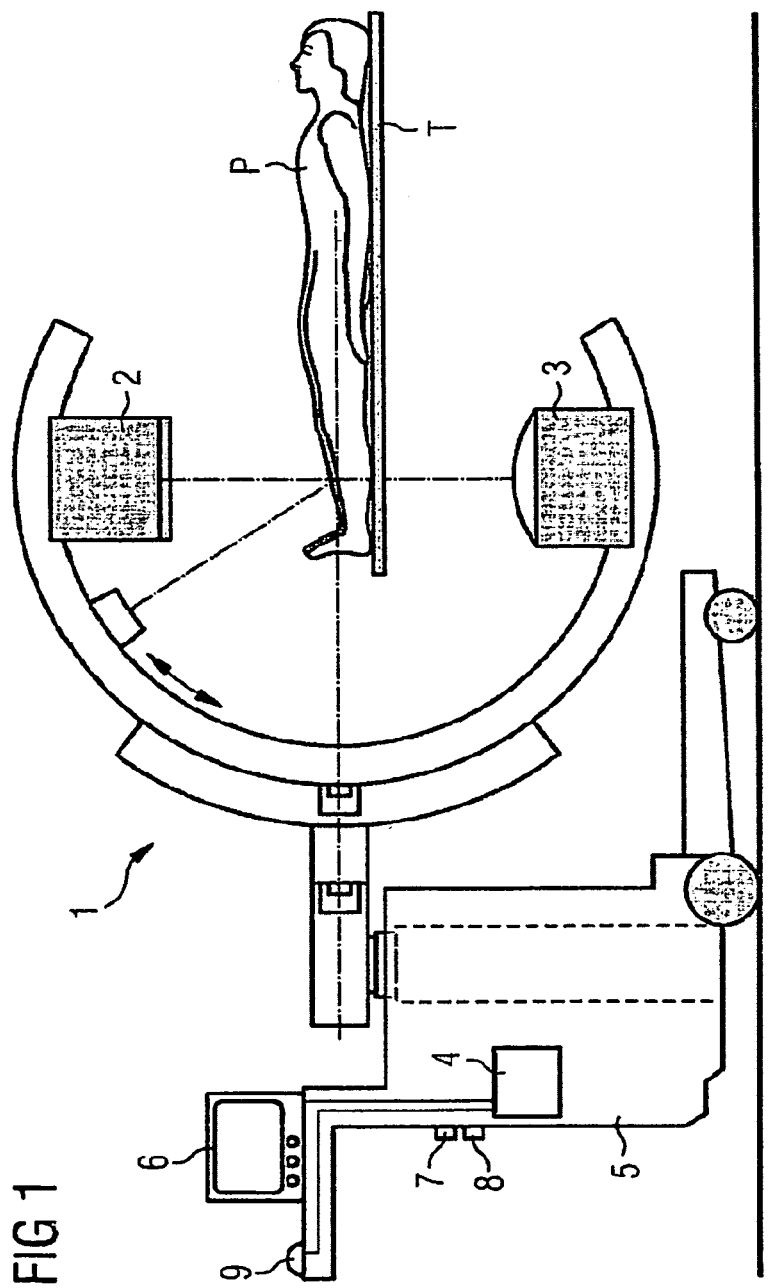
FIG. 1 shows in a side view a C-arm X-ray device which has a touchscreen embodied according to the invention as operator control element.

FIG. 1 diagrammatically shows a side view of a C-arm X-ray device 1 wherein a patient P is lying on a table T which is transparent to X-ray radiation and is vertically adjustable by means of a mechanism that is not shown in further detail. Various adjustment options of the C-arm X-ray device 1 with the X-ray radiation source 2 and the radiation detector 3 as well as by adjustment of the table T enable the patient P to be radiologically examined in the multifarious ways. The different elements of the X-ray device 1 are controlled in this case via a computer 4 which is disposed within a diagrammatically represented device carriage 5.

On the top of the device carriage 5 there is also a display 6 which can be used on the one hand for displaying examination results, but in particular is also used as a touchscreen for operating and controlling the X-ray device 1. In order to input information a user of the X-ray device 1 must therefore touch the touchscreen 6 which is formed by means of a touch-sensitive film which is applied as an overlay onto a TFT display. The electrical signals generated when the film is touched are then analyzed in order to establish the precise point at which the screen was touched so that the signals of a specific item of input information which corresponds to the representation on the underlying TFT display can be assigned.

Since signs of wear and minor changes in the properties of the touch-sensitive film can lead over time to variations in the signals generated when the screen is touched, it is necessary to calibrate the touchscreen 6 from time to time. Typically, this is accomplished by input of a corresponding command with the aid of a PC keyboard or PC mouse. However, this possibility does not exist in the case of the illustrated X-ray device 1, since essentially only the touchscreen 6 itself is available as an operator control element. The only other input elements of the X-ray device 1 are formed by a central on/off key 7, a service key 8 (explained in more detail later) for activating a service mode, and an emergency shutoff switch 9. Although it would be conceivable to provide further keys for activating a calibration routine on the X-ray device 1, this should be avoided.

The solution according to the invention permits the calibration routine to be initiated without the requirement for additional keys. This will be explained in more detail below with reference to FIG. 2.

Figure 2:
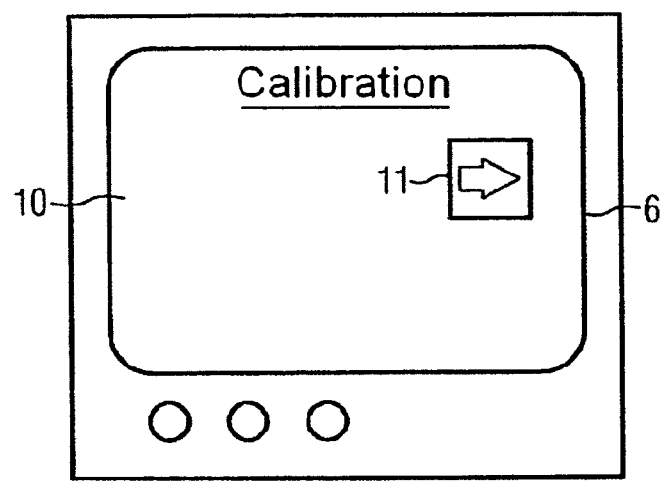
FIG. 2 shows an enlarged representation of the touchscreen at the start of the service mode.

Here, FIG. 2 shows the touchscreen 6 at the start of a so-called service mode which was started by an actuation of the service key 8. Said service mode is usually used only by the maintenance personnel of the X-ray device 1 in order to set certain operating parameters of the X-ray device 1 and carry out maintenance measures. In addition it is also possible to activate the service mode automatically whenever the controller detects operating states which point to a decalibration of the touchscreen or to some other service need.

According to the invention it is henceforth provided that initially the calibration query shown in FIG. 2 is to be issued every time the service mode is started. In this state the entire screen surface 10 of the touchscreen 6 essentially serves as an activation element for invoking the calibration routine. Thus, if a user of the X-ray device 1 or, as the case may be, the maintenance personnel would like to perform a calibration of the touchscreen 6, it is sufficient to touch the screen essentially at any point. Even in the case of a completely decalibrated touchscreen it is thus made possible for the calibration routine to be called without the actuation of an additional input element. It is therefore possible to dispense with the input means previously required therefor such as, for example, a keyboard or a PC mouse.

Since, however, a recalibration of the touchscreen 6 is not absolutely essential at every start of the service mode, it can be provided that there is also the possibility for the user to skip the calibration routine. For this purpose a specific predefined smaller area of the screen 10 is provided as a Next key 11 or bypass key or, as the case may be, element, in which case, when the corresponding area of the screen surface is touched, the calibration routine is skipped and the actual service mode is started immediately. Accordingly, if the touchscreen is already adequately calibrated, the user can easily switch directly to the service mode by touching the Next key 11.

The advantage of this embodiment is that if the touchscreen is decalibrated the user automatically activates the calibration routine even though he or she initially believes he or she is actuating the Next key 11. In other words, it is ensured by means of the embodiment according to the invention that at the start of the service mode a calibration of the touchscreen 6 is fundamentally performed insofar as this is necessary due to a decalibration. The calibration is then performed in the known manner, i.e. certain predefined areas of the screen are touched and the signals generated in the process evaluated.

It should be noted that it would also be conceivable to activate the selection option shown in FIG. 2 for invoking the calibration routine as a matter of course every time the X-ray device 1 is started. However, since a calibration of the touchscreen is not absolutely essential every time the device is started, it is sufficient to restrict the selection option to the start of the service mode. In addition it would also be conceivable for the selection option to be terminated automatically after a certain waiting period has elapsed and for a switch to be made to the service mode or, as the case may be, the normal operating mode without the calibration being performed. In this case it would also be possible to dispense with the illustrated Next key 11.

The solution according to the invention therefore permits the reliable activation of the requisite routine for calibrating the touchscreen. In particular no additional input element is required therefor, so the extension according to the invention can easily be implemented in the control software of the device.

The invention claimed is:

1. A touch screen control element for operating a medical device, comprising:
a touch-sensitive screen surface that controls operation of the medical device, wherein the medical device does not comprise an additional input device and is operated by the touch-sensitive screen surface without use of the additional input device;
a service key for activating a service mood of the device; and an activation element for activating a calibration routine during a start phase of the service mode of device where the entire screen surface of the touch-sensitive screen serves as the activation element for activating the calibration routine during the start phase of the service mode of the device without the use of the additional input device.

2. An operator control element for operating a medical device, comprising:
   a touchscreen having a touch-sensitive screen surface and wherein a calibration routine is provided for calibrating the touchscreen that controls operation of the medical device, wherein the medical device does not comprise an additional input device and is operated by the touch-sensitive screen surface without use of the additional input device;
   a service key for activating a service mood of the device; and
   an activation element for activating the calibration routine during a start phase the service mode of the device without the use of the additional input device,
   wherein the touchscreen serves as the activation element for activating the calibration routine during the start phase of the service mode of the device.

3. The operator control element as claimed in claim 2, wherein an entire screen surface of the touchscreen is the activation element for activating the calibration routine.

4. The operator control element as claimed in claim 2, wherein a first area of the screen surface of the touchscreen serves as the activation element for activating the calibration routine.

5. The operator control element as claimed in claim 4, further comprising a bypass key arranged in a second area of the screen surface of the touchscreen for skipping the calibration routine by touching the bypass key.

6. The operator control element as claimed in claim 5, wherein the second area of the screen surface encompasses a smaller surface area than the first area of the screen surface.

7. A method for operating a medical device, by a touchscreen, comprising:
   providing a calibration routine for calibrating the touchscreen that controls operation of the medical device without use of an additional input device;
   activating a service mood of the medical device by actuating a service key; and
   activating the calibration routine during a start phase of the service mode of the medical device by a user touching a portion of the entire screen surface of the touchscreen without the use of the additional input device,
   wherein the touchscreen serves as an activation element for activating the calibration routine during the start phase of the service mode of the device.

8. The method as claimed in claim 7, wherein the calibration routine is activated during a start phase of the device and during the start phase of a service mode of the device.

9. The method as claimed in claim 8, wherein the service mode is invoked with the aid of a separate operator control element of the device.

10. The method as claimed in claim 9, wherein the entire screen surface of the touchscreen serves as an activation element for activating the calibration routine.

11. The method as claimed in claim 10, wherein a portion of the screen surface of the touchscreen serves as a bypass element for omitting the calibration routine.

* * * * *